US00PP25944P3

(12) United States Plant Patent
Tristram

(10) Patent No.: US PP25,944 P3
(45) Date of Patent: Sep. 22, 2015

(54) ***SEDUM* PLANT NAMED 'PIZZAZZ'**

(50) Latin Name: *Sedum spectabile*
Varietal Denomination: Pizzazz

(71) Applicant: David R. Tristram, Arundel (GB)

(72) Inventor: David R. Tristram, Arundel (GB)

( * ) Notice: Subject to any disclaimer, the term of this patent is extended or adjusted under 35 U.S.C. 154(b) by 95 days.

(21) Appl. No.: 13/987,473

(22) Filed: Jul. 29, 2013

(65) Prior Publication Data

US 2014/0041089 P1 Feb. 6, 2014

Related U.S. Application Data

(60) Provisional application No. 61/742,080, filed on Aug. 1, 2012.

(51) Int. Cl.
*A01H 5/02* (2006.01)

(52) U.S. Cl.
USPC ..... Plt./479
CPC ..... *A01H 5/02* (2013.01)

(58) Field of Classification Search
USPC ..... Plt./479
CPC ..... A01H 5/02
See application file for complete search history.

(56) References Cited

PUBLICATIONS

Garden Center Magazine, Dec. 3, 2012.*

* cited by examiner

*Primary Examiner* — Keith O. Robinson
(74) *Attorney, Agent, or Firm* — Barbara Campbell; Bethany R. Roahrig; Cochran Freund & Young, LLC

(57) ABSTRACT

A new and distinct variety of *Sedum* named 'Pizzazz' that is characterized by clump forming habit, thick mid-green colored leaves, and flowers with long petals which are mid-pink in color in summer, becoming bright cerise at peak of flowering in late summer and early fall, and aging to deep ruby before senescence.

1 Drawing Sheet

Genus and species: *Sedum spectabile.*
Variety denomination: 'Pizzazz'.

BACKGROUND OF THE NEW PLANT

The present invention relates to a new variety of stonecrop grown as an ornamental for use in containers and for growing in the garden border or landscape. The new invention from the family Crassulaceae is known botanically as *Sedum spectabile* and will be referred to hereinafter as 'Pizzazz'.

'Pizzazz' arose as a seedling which the inventor selected in 2005 from many seedlings raised from the self-fertilization of *Sedum* 'Neon' (unpatented). In comparison with other seedlings, the selected seedling, 'Pizzazz' exhibited the brightest flower color and the most compact plant shape.

'Pizzazz' was first asexually propagated in 2008 by the inventor in Arundel, West Sussex, United Kingdom. Asexual propagation was accomplished using stem cuttings. Since that time, under careful observation, the distinguishing characteristics of 'Pizzazz' have been determined stable and uniform, and to reproduce true to type in successive generations of asexual propagation.

SUMMARY

'Pizzazz' exhibits clumping habit with mid-green foliage. The flowers of 'Pizzazz' open mid-pink in color in summer, becoming bright cerise at peak flowering in late summer and early fall. During peak flowering, the stamens of 'Pizzazz' are prominently exserted and brightly cerise in color. Plants of 'Pizzazz' achieve 35.0 cm to 45.0 cm in height and 30.0 cm to 40.0 cm in width after one year of growth, and reach 45.0 cm in height and 45.0 cm in width at maturity. Cultural requirements include free-draining soil, full sun, and minimal water.

'Pizzazz' is susceptible to snails, slugs, and mildew. Spraying is recommended in areas of high humidity to prevent mildew, and use of snail bait is recommended to prevent damage from snails and slugs. 'Pizzazz' is hardy in USDA Zone 5.

The following traits have been repeatedly observed and represent the distinguishing characteristics of the new *Sedum* variety named 'Pizzazz'. These traits in combination distinguish 'Pizzazz' from all other existing varieties of *Sedum* known to the inventor. 'Pizzazz' has not been tested under all possible conditions. Phenotypic differences may be observed with variations in environmental, climatic, and cultural conditions.

1. Plants of 'Pizzazz' exhibit a compact clump-forming growth habit.
2. The foliage of 'Pizzazz' is mid-green in color.
3. During peak flowering, the inflorescence of 'Pizzazz' is bright cerise in color.
4. During peak flowering, the stamens of 'Pizzazz' are prominently exserted and are bright cerise in color.
5. The flowers of 'Pizzazz' open mid-pink in summer, becoming bright cerise at peak of flowering in late summer, aging to deep ruby before senescence.
6. At one year of age, plants of 'Pizzazz' are 35.0 cm to 45.0 cm in height and 30.0 cm to 40.0 cm in width.
7. At maturity, plants of 'Pizzazz' are 45.0 cm in height and width.
8. 'Pizzazz' blooms from summer to fall.
9. 'Pizzazz' is hardy to USDA Zone 5.

COMPARISON WITH PARENTAL LINE AND KNOWN VARIETY

'Pizzazz' is unique and distinguishable from any other *Sedum* known to the inventor. The closest comparison plant is

*Sedum* 'Autumn Joy' (unpatented). Whereas the flowers of 'Autumn Joy' open dark pink and aging to brick-red, the flowers of 'Pizzazz' flowers open mid-pink in color in summer, becoming bright cerise at the peak of flowering in late summer and early fall, and aging to deep ruby. In addition, the growth habit of 'Pizzazz' is more compact and shorter than 'Autumn Joy'.

When compared with the parental variety 'Neon', 'Pizzazz' exhibits brighter flower colors and a more compact habit.

BRIEF DESCRIPTION OF THE PHOTOGRAPH

The accompanying photograph illustrates a close-up of 'Pizzazz' showing the colors of its foliage and flowers as true as it is reasonably possible to obtain in colored reproductions of this type. The photograph depicts the typical and characteristic bright cerise inflorescences of 'Pizzazz' when the individual flowers in the inflorescence are semi-open to fully-open. The plants in this photograph are approximately one-year-old and have been grown outdoors in 3-liter containers in Arundel, West Sussex, United Kingdom. The photograph was taken in September 2010.

BOTANICAL DESCRIPTION OF THE PLANT

The following is a detailed botanical description of the new *Sedum* variety named 'Pizzazz'. Observations, measurements, values and comparisons were collected in Santa Barbara, Calif., in July 2013 from 18-month-old plants grown outdoors in the border soil. Color determinations are made in accordance with The 2007 Royal Horticultural Society Colour Chart from London, England, except where general color terms of ordinary dictionary significance are used. The growing requirements of the new variety 'Pizzazz' are similar to the species.

Botanical classification:
- *Family.*—Crassulaceae.
- *Genus and species.*—*Sedum spectabile.*
- *Denomination.*—'Pizzazz'.
- *Common name.*—Stonecrop.

Parentage: Selected seedling raised from the self-fertilization of *Sedum* 'Neon' (unpatented).

Plant:
- *Habit.*—Clump forming.
- *Commercial category.*—Succulent.
- *Use.*—Container and border.
- *Suggested commercial container size.*—2-liter container.
- *Propagation method.*—Stem cuttings.
- *Rooting system.*—Fine and fibrous.
- *Root color.*—Ranges between N167C and N167D.
- *Vigor.*—Moderate.
- *Crop time* (*range*).—8 to 16 weeks from a cutting to a 5.0 cm liner pot and 16 to 24 weeks from a liner pot a finished 2-liter container plant in flower.
- *Plant dimensions* (*first year*).—35.0 cm to 45.0 cm in height and 30.0 cm to 40.0 cm in width.
- *Plant dimensions* (*at maturity*).—45.0 cm in height and width.
- *Cultural requirements.*—Grow in free-draining soil and full sun, with minimal water.
- *Pest and disease resistance.*—None known to the inventor.
- *Disease susceptibility.*—Powdery Mildew (*Podosphaera xanthii*).
- *Pest susceptibility.*—Common garden snails (*Helix aspera*), slugs (gastropods, Order *Pulmonata*).
- *Hardiness.*—USDA Zone 5.

Stem, lateral branches:
- *Stem height.*—8.0 cm to 10.0 cm.
- *Stem diameter.*—3.0 cm to 4.0 cm.
- *Lateral branch length.*—20.0 cm to 30.0 cm.
- *Lateral branch diameter.*—5.0 mm to 10.0 mm at the stem.
- *Lateral branch quantity.*—16.
- *Lateral branch internode distance* (*average*).—0.50 cm.
- *Stem and branch color.*—145A.
- *Stem and branch surface.*—Glabrous.
- *Stem and branch strength.*—Strong.
- *Stem and branch texture.*—Semi-glossy.

Foliage:
- *Leaf quantity* (*range*).—35 to 45 per stem.
- *Leaf attachment.*—Sessile.
- *Leaf arrangement.*—Alternate.
- *Leaf texture* (*abaxial and adaxial surfaces*).—Rubbery.
- *Leaf division.*—Simple.
- *Leaf margin.*—Entire.
- *Leaf surface* (*abaxial and adaxial*).—Glabrous and semi-glossy.
- *Leaf shape.*—Elliptic.
- *Leaf length* (*average*).—6.0 cm.
- *Leaf width* (*average*).—3.0 cm.
- *Leaf thickness.*—3.0 mm to 4.0 mm.
- *Leaf color* (*both surfaces*).—143C with cream pink coloration to leaf edges in hot dry conditions.
- *Leaf apex* (*range*).—Acute to rounded.
- *Leaf base.*—Truncate.
- *Venation.*—Pinnate.
- *Vein color* (*abaxial and adaxial surfaces*).—143C.

Inflorescence:
- *Inflorescence type.*—Flat topped cyme.
- *Blooming season.*—Summer to fall.
- *Inflorescence quantity* (*average*).—16.
- *Inflorescence dimensions* (*fully expanded*).—5.0 cm to 10.0 cm in height, 12.0 cm to 18.0 cm in width.
- *Flower quantity per inflorescence.*—Very numerous; approximately 250 to 300.
- *Flower dimensions* (*fully expanded*).—6.0 mm in depth, 10.0 mm in diameter at the sepal apices.
- *Flower aspect.*—Facing upward.
- *Fragrance.*—None observed.
- *Lastingness of individual flowers on the plant.*—10 to 14 days before senescence.
- *Persistent or self-cleaning.*—Persistent.

Bud:
- *Bud shape.*—Ovoid.
- *Bud dimensions.*—3.0 mm in length and 2.0 mm in width.
- *Bud surface.*—Glabrous.
- *Bud apex.*—Acute.
- *Bud base.*—Rounded.
- *Bud color.*—N155C.

Petals:
- *Petal quantity.*—5 in number.
- *Petal color.*—Ranges between N57A and N57B.
- *Petal shape.*—Oval.
- *Petal apex.*—Acute.
- *Petal base, fused or unfused.*—Unfused.
- *Petal margin.*—Entire.

*Petal dimensions.*—7.0 mm to 8.0 mm in length and 2.0 mm in width.

*Petal surface texture* (*abaxial and adaxial*).—Glabrous.

Sepals:

*Sepal quantity.*—5 in number.

*Sepal shape.*—Oval.

*Sepal color.*—N144A.

*Sepal apex.*—Acute.

*Sepal base, fused or unfused.*—Unfused.

*Sepal margin.*—Entire.

*Sepal dimensions.*—1.0 mm in length and 0.50 mm in width.

*Sepal surface texture* (*abaxial and adaxial*).—Glabrous.

Peduncle:

*Peduncle shape.*—Cylindrical.

*Peduncle color.*—N144A.

*Peduncle surface texture.*—Glabrous.

*Peduncle dimensions.*—2.50 cm in length and 3.0 mm in diameter.

*Peduncle angle*.—Varies between 0 degrees (that is, in line with the stem) and 45 degrees away from the direction of the stem.

*Peduncle strength.*—Moderately strong; may break away under heavy wind or rain.

Pedicel:

*Pedicel shape.*—Cylindrical.

*Pedicel color.*—N144A.

*Pedicel surface texture.*—Glabrous.

*Pedicel dimensions.*—0.50 cm in length and 1.0 mm in width.

*Pedicel angle*.—Varies between 0 degrees (that is, in line with the peduncle) and 45 degrees away from the direction of the peduncle.

*Pedicel strength*.—Moderately strong.

Reproductive organs:

*Stamens.*—10 in number, 5 short, approximately 2.0 mm in length and attached to petal base; 5 long, prominently exserted, approximately 6.0 mm to 10.0 mm in length, alternating with petals.

*Filament color* (*short stamens*).—N57A.

*Filament color* (*long stamens*).—N57A becoming paler, almost white, N155B, towards the anthers.

*Anthers.*—Shape ellipsoid, 1.5 mm in length, 1.0 mm in width, color 60C.

*Pollen*.—Sparse or absent; has not been observed.

*Pistils.*—5 in number, length is 6.0 mm to 10.0 mm.

*Style*.—Length is less than 1.0 mm, color is N57A.

*Stigma*.—Shape is conical and color is N57A.

*Ovary*.—Not observed.

Seed: Fine, ovoid, less than 0.05 mm in length.

I claim:

1. A new and distinct cultivar of *Sedum* plant named 'Pizzazz' as described and illustrated herein.

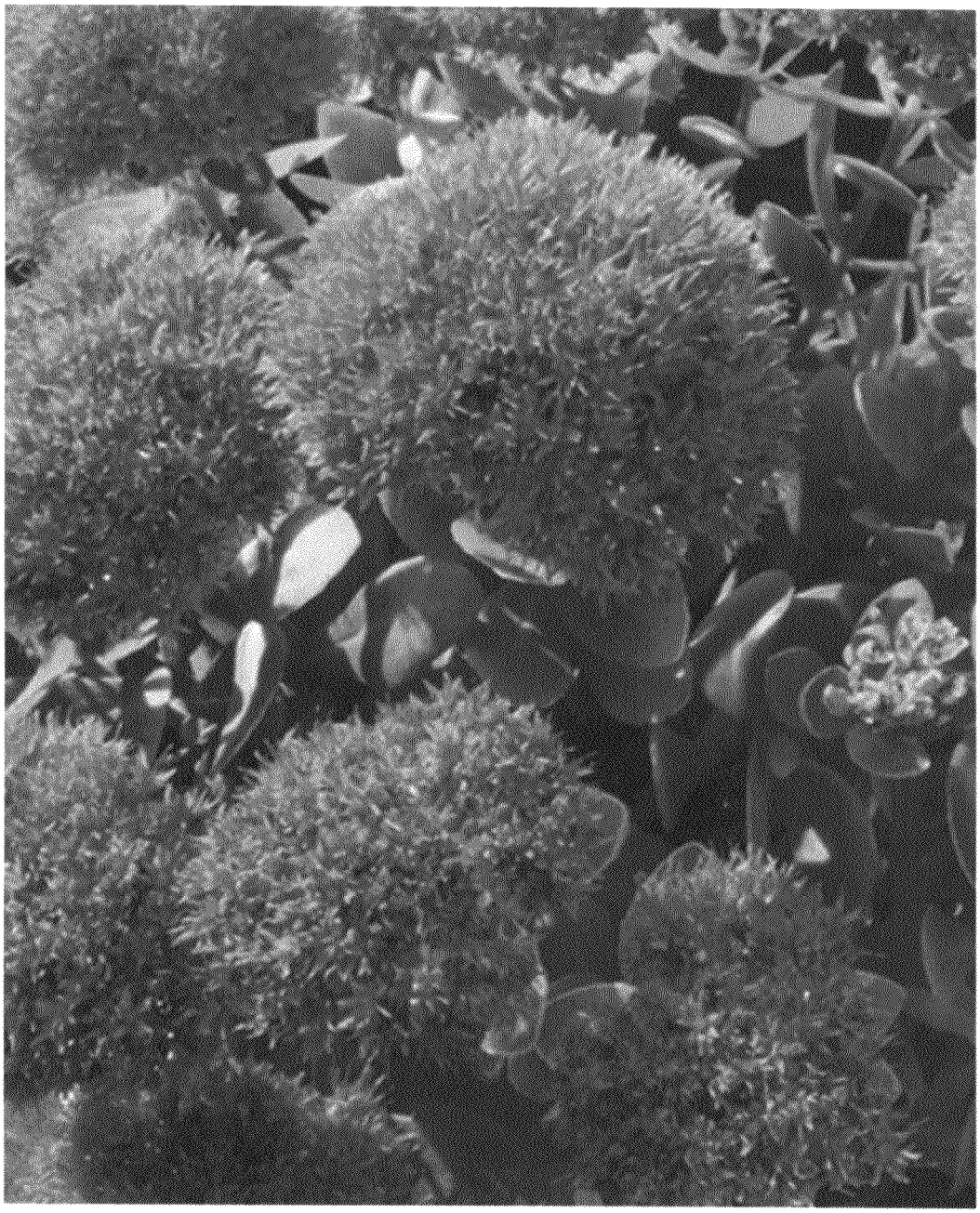

* * * * *